US00PP11026P

United States Patent [19]

Adams et al.

[11] Patent Number: Plant 11,026

[45] Date of Patent: Aug. 3, 1999

[54] GLOBBA PLANT NAMED 'BLUSHING MAIDEN'

[76] Inventors: Gregory A. Adams, P.O. Box 4245; Mark L. Collins, P.O. Box 4099, both of Hilo, Hi. 96720

[21] Appl. No.: 09/001,818

[22] Filed: Dec. 31, 1997

[51] Int. Cl.[6] ..... A01H 5/00

[52] U.S. Cl. ..... Plt./263

[58] Field of Search ..... Plt./68.1, 263

*Primary Examiner*—Howard J. Locker
*Assistant Examiner*—Kent L. Bell
*Attorney, Agent, or Firm*—Seth M. Reiss

[57] ABSTRACT

A new and distinct variety of a Globba hybrid characterized by a two-tone blend of pink and white bracts with mostly transparent bracteoles with pink streaking and yellow green tips as within the inflorescence. The foliage displays reddish underleaves.

2 Drawing Sheets

CROSS-REFERENCE TO RELATED APPLICATIONS

This application is co-pending with U.S. Plant Patent application Ser. Nos. 09/002,231, 09/002,238, and 09/002,239 drawn to cultivars 'Pristina Pink', 'Purest Angel', and 'Ruby Queen', respectively. Being of the same Genus and species, all four cultivars demonstrate similar growth habits and life cycles. The plants are distinct, one from the other, in their bract color; the instant cultivar exhibiting persistent white and pink two-tone bracts compared with the light pink bracts of 'Pristina Pink', the white bracts of 'Purest Angel', and the dark bracts of 'Ruby Queen'.

BACKGROUND

This new Globba 'Blushing Maiden' was selected by applicants from the seedling progeny from a cross of unknown parents of *Globba winitii* by applicants at Jungle Jewels, Hi., Kurtistown Hi., USA. This particular seedling was selected by the applicants in 1994 for propagation and testing because of the distinctive white and pink two-tone bracts and reddish underleaves. The selected plant was propagated asexually by cuttings and tissue culture and successive generations maintained the unique features of this new variety. Tissue culture was performed in a lab in Apopka, Fla. The plant was then grown to maturity in greenhouses in Kurtistown, near Hilo, Hi.

BRIEF SUMMARY OF INVENTION

'Blushing Maiden' is a low growing deciduous herbaceous perennial with multiple showy pendulous inflorescences. The life cycle of this variety consists of numerous reed like leafy stems emerging in April–May with vigorous growth until flowering commences from July through November with persistent white and pink two-tone bracts. In December complete foliar senescence will proceed with a rest period until the following growing season, unless supplemental lighting is applied, therefore extending the flowering period.

BRIEF DESCRIPTION OF PHOTOGRAPHS

Figure 1:
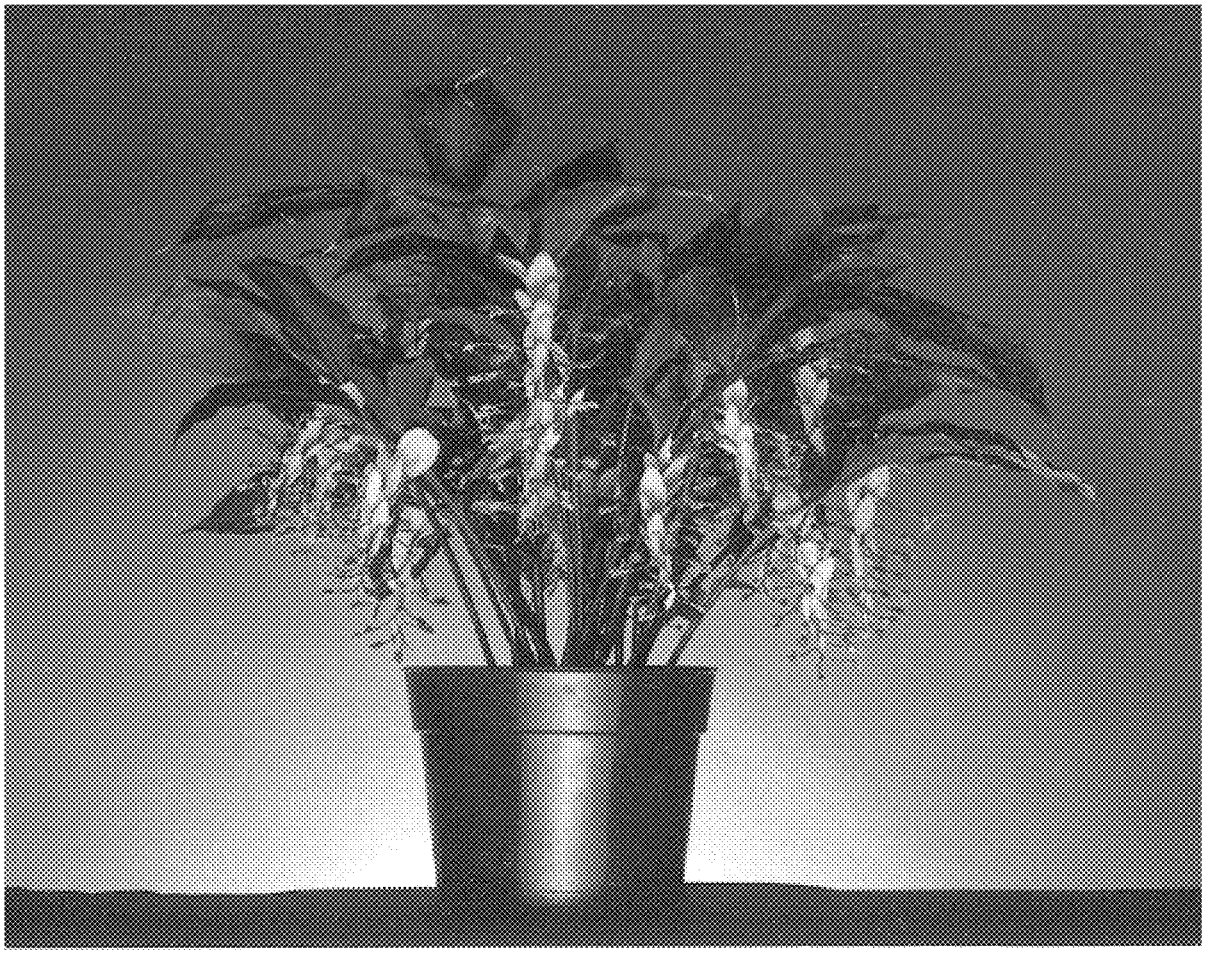

The accompanying color photographs show:

FIG. 1. Depicts the plant form and size and the display of inflorescences.

Figure 2:
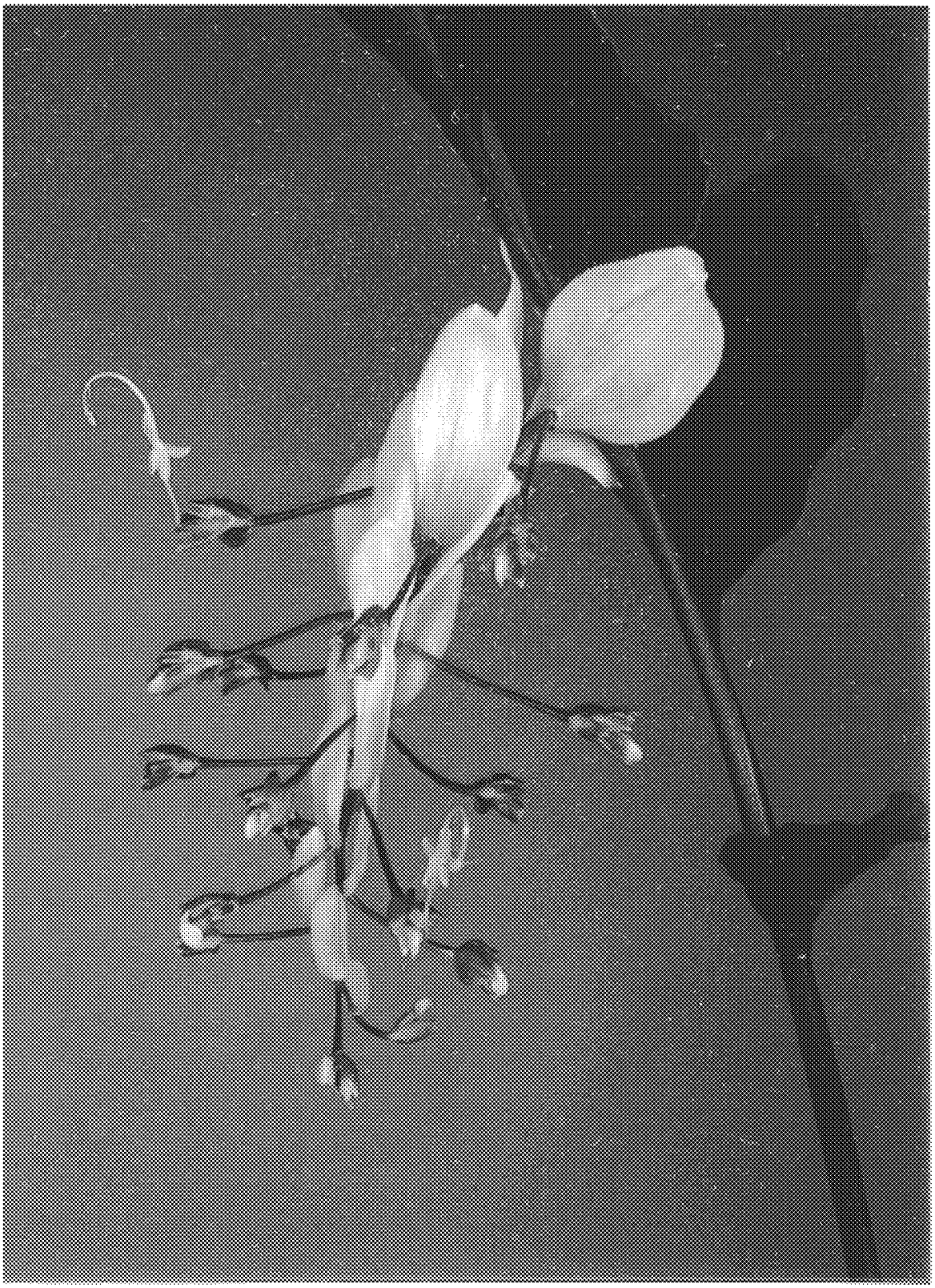

FIG. 2. Depicts a side view of a fully open inflorescence depicting bract color of 'Blushing Maiden', having flowers extending out of two of the corollas.

The colors are as nearly true as reasonably possible in color illustrations of this type.

DETAILED BOTANICAL DESCRIPTION

In the following botanical description color references are made to The Royal Horticultural Society Colour Chart. Descriptions are based on observations made during 1996 of randomly selected well fertilied clones, grown from fully developed rhizomes, which will yield maximum height and maturity of this variety. 'Blushing Maiden' was grown in greenhouse conditions in Kurtistown, Hi. under 55% shaded nursery conditions.

Name: 'Blushing Maiden'.
Botanical name: *Globba winitii.*
Family: Zingiberaceae.
Commercial use: Potted Flowering Ornamental Plant.
Botanical description: Perennial herb with slender fleshy rhizomes, fibrous roots and reed-like leafy stems. Leaves elliptic-lanceolate, attenuate at base, alternate. The top two terminate leaves per pseudostem appear petioled, while the lower leaves are sheathed and appear more sessile in nature. Inflorescence a pendulous terminal raceme, bracts showy; flowers born in cincinni on slender branchlets arising from axils of bracts; bracteoles ovate and open to base; calyz funnelform, 3-lobed; corolla exceeding calyx; 3 petals, small subequal, posterior petal spurred; lip fused into tube with stamen above attachment of lateral staminodes and petals, 2 lobed deflexed; staminodes petaloid, equal or exceeding petals; 1 fertile stamen, filament long and curved, anther with two small triangular appendages on each side; ovary 1 celled with several ovules. The number of bracts and bracteoles per inflorescence vary with the maturity of the cultivar. An immature cultivar, during the flowering period of its second growing season, can be expected to exhibit, on average, between 5 and 12 bracts per inflorescence. A matue cultivar, during the flowering period of its third and subsequent growing seasons, may exhibit, on average, between 12 and 20 bracts per inflorescence and between 12 and 20 bracteoles per inflorescence. Flowers last a single day. On average, 6 to 8 actual flowers are produced per branchlet in cincinni each growing season. In a given growing season, an immature plant may exhibit anywhere from 35 to 84 flowers per inflorescence, while a mature plant exhibits from 84 to 140 flowers per inflorescence. Fruit; a small dehiscent capsule with arillate seed with hemispherical protruberances on the outer exocarp.

Plant characteristics:

*Average mature height.*—38 cm.

*Average mature spread.*—55 cm.

*Leaf attitude.*—Arching.

*Leaf length.*—12–16 cm.

*Leaf width.*—4–5.5 cm.

*Leaf color* (*surface and midrib*).—Upper: Green 131A and greyed purple group blended. Lower: Greyed purple 187B and green group blended.

*Leaf texture.*—Smooth.

*Leaf shape.*—Elliptic Lanceolate.

*Flowering season.*—July through November.

*Inflorescence overall length.*—11–13 cm.

*Bract basal* (*largest*).—3.7 cm×2.5 cm.

*Bract apical* (*smallest*).—1 cm×0.8 cm.

*Bract color.*—Upon maturity a two-tone blend of red purple 70B at the base fusing to white 155C at tip of each of the larger bracts. Smaller bracts at the apical end of the inflorescence are mostly absent of white.

*Bracteoles color.*—Mostly transparent with red purple 59C streaking with a yellow green 144C tip.

*Raceme and raceme branchlet color.*—Greyed purple 184A.

*Flower overall height.*—2.2 cm.

*Anther with appendages width.*—0.5 cm.

*Stamen length.*—1.5 cm.

*Flower color.*—Yellow Orange 17B.

*Disease resistance.*—It is not known whether the instant cultivar exhibits special resistance to diseases typical of Globba.

We claim:

1. A new and distinct variety of Globba plant named 'Blushing Maiden', substantially as herein shown and described, characterized particularly as to novelty by the unique combination of white and pink two-tone bracts and reddish under leaves along with its profuse flowering habit.

* * * * *